(12) United States Patent
Zacouto

(10) Patent No.: US 6,692,495 B1
(45) Date of Patent: Feb. 17, 2004

(54) VERTEBRAL FIXATOR AND ARTICULATION

(76) Inventor: Fred Zacouto, 16 rue de la Convention, Paris (FR), 75015

(*) Notice: Subject to any disclaimer, the term of this patent is extended or adjusted under 35 U.S.C. 154(b) by 167 days.

(21) Appl. No.: 09/686,797

(22) Filed: Oct. 12, 2000

(30) Foreign Application Priority Data

Oct. 14, 1999 (FR) .............................. 99 12812

(51) Int. Cl.⁷ .................................. A61F 2/44
(52) U.S. Cl. ...................... 606/61; 623/17.12
(58) Field of Search ................ 606/61; 623/17.12

(56) References Cited

U.S. PATENT DOCUMENTS

| | | | |
|---|---|---|---|
| 4,932,975 A | * | 6/1990 | Main et al. ............... 606/61 |
| 5,002,576 A | | 3/1991 | Fuhrmann et al. |
| 5,236,460 A | | 8/1993 | Barber |
| 6,419,704 B1 | * | 7/2002 | Ferree .................. 623/17.12 |

FOREIGN PATENT DOCUMENTS

| | | |
|---|---|---|
| EP | 0 346 269 | 12/1989 |
| WO | WO 94/04100 | 3/1994 |
| WO | WO 00/13620 | 3/2000 |

* cited by examiner

*Primary Examiner*—Kevin Shaver
*Assistant Examiner*—Candice C. Melson
(74) *Attorney, Agent, or Firm*—Muserlian, Lucas and Mercanti (57) ABSTRACT

The invention relates to an intervertebral and intravertebral fixation making exclusive use of this space. The vertebral fixation uses rods or screws perpendicular to the articular faces of the vertebrae, which rods or screws are introduced by the conventional posterior or lateral spinal surgical routes. An artificial discal articulation can be placed between these vertebral fixators using these same posterior routes, the fixation being adjustable or self-adjustable according to movements of the patient. Surgical implantation thus becomes quick, without subjecting the patient to a major intervention.

23 Claims, 9 Drawing Sheets

VERTEBRAL FIXATOR AND ARTICULATION

The present invention relates to a vertebral fixator and more particularly to an intervertebral/intravertebral fixator which may include an artificial discal articulation forming a disc prosthesis.

To combat severe vertebral and distal instability, particularly as a result of degeneration, which shows up as pain and stiffness which may be accompanied by compression of the spinal nerves and/or spinal cord, it is known practice for fixator devices known as "cages" to be introduced into the intervertebral space. These cages, which generally consist of a small, holed hollow cylinder, are implanted by conventional posterior spinal surgical routes and usually require a bone graft, particularly a self-graft, to fix them rigidly. Implantation by the posterior route is advantageous because this is a relatively minor surgical intervention well tolerated by patients, particularly the elderly, and well mastered by surgeons. The cages do, however, present major drawbacks. On the one hand, they achieve total rigidity between the two vertebral discs that they interconnect, consequently eliminating any mobility at this point. When the cages are implanted in a number of intervertebral spaces, the entire regional vertebral column looses its natural suppleness or flexibility. In this case, the discs of the adjacent vertebral stages are overloaded and, in turn, will require arthrodesis. On the other hand, the use of cages entails a bone graft or osteosynthesis to fix the cages in the intervertebral space and fuse the vertebrae. These cages rarely provide sufficient stability and entail the additional fixing of one or more bulky posterior arthrodeses (metal plates or rods) on the vertebral column, which are also often necessary to avoid immobilizing the patient after the operation. Furthermore, these cages do not enlarge the height of their intervertebral space as much as they could, because they are small and the grafted bone matter does not exert a force that separates the vertebrae.

WO 00/13620 describes a pair of cages each of which is formed of two half cages between which a deformable material with damping properties is located. These cages have the conventional drawbacks of cages are regards fixing and bone grafting or osteosynthesis.

It is also known practice for devices with articulation, known as artificial discs, generally consisting of curved (convex or concave) elements capable of sliding one with respect to the other to be introduced into the intervertebral space. These devices are not fixators and are therefore not generally effective against vertebral instabilities. Furthermore, their effectiveness as an articulation is limited over time, generally to a few years, because after a certain length of time the relative movement between the two elements is disturbed. What is more, the amount of mobility, the geometry and/or the dimensions of these devices are not adjustable, particularly during and after implantation, which means that anatomical tailoring is not possible. A major drawback of these devices also lies in the necessity to resort to implantation via a non-posterior route. For the elderly, this then is a very major surgical intervention.

By way of example, such implants are described in EP-A-0820731 and in the pending American application 09/200855 and its parent application 08/897673, the contents of which documents are incorporated herein by reference. Despite of the very attractive properties regarding the possibilities of damping or adjustment after implantation, such artificial discs exhibit the other drawbacks mentioned hereinabove. Other intervertebral prostheses exhibiting the same kinds of drawbacks are described in EP-A-0346269.

WO 94/04100 describes an intervertebral discal prosthesis equipped with means of attachment into the adjacent vertebral bodies but also entailing a difficult surgical approach and furthermore requiring the intervertebral space to be opened up significantly during the fitting operation.

There also exist vertebral prostheses whose role is not to form a disc but to replace one or more vertebrae, forming an arthrodesis thereat. An implant such as this is described, for example, in U.S. Pat. No. 5,236,460, which describes an axially expandable vertebral implant with spikes capable of penetrating the vertebral bodies upon expansion. These prostheses are obviously used in far more major operations than those aimed at replacing a disc between two vertebral bodies.

The object of the present invention is to provide a vertebral fixator which does not reproduce the aforementioned drawbacks.

In particular, the object of the present invention is to provide a vertebral fixator which provides perfect fixation without the need for a bone graft.

In particular, the object of the present invention is to provide a vertebral fixator which may include a discal articulation which can afford some mobility and/or viscoelasticity.

Another object of the present invention is to provide a vertebral fixator such as this which can preferably be implanted by a strictly posterior route.

A further object of the present invention is to provide a vertebral fixator such as this, in which the degree of discal articulation mobility can be adjusted before, during and/or after implantation of the fixator.

Another object of the present invention is to provide a vertebral fixator such as this which can be removed, if necessary, preferably using the same posterior surgical route.

A further object of the present invention is to provide an intervertebral fixator such as this which can be connected to posterior fixator devices implanted on the posterior sides of the vertebral column. Such posterior devices advantageously comprise the adjustable devices described in documents EP-0 820 731 and FR-98 05549.

The subject of the present invention is therefore a vertebral fixator intended to be implanted between two adjacent vertebrae and consisting of fixator elements arranged exclusively in the intervertebral space defined between the said vertebrae and of fixator members fixed to the inside of the said vertebrae.

Advantageously, the said fixator comprises one essentially rigid first element fixed to the articular face of one of the two vertebrae, and one essentially rigid second element fixed to the articular face of the other vertebra, the said essentially rigid first and second elements being connected by at least one intermediate element.

Advantageously, the said essentially rigid first and second elements are plates comprising holes, the said plates each being arranged in the intervertebral space against the articular face of a respective vertebra so that the fixation members such as rods or screws are passed through the said holes and fixed, particularly screwed, into the respective vertebra.

According to a particular embodiment of the invention, the fixation members are screwed by means of a rotary rod introduced approximately radially into the intervertebral space, a system of rotary gearwheels being provided to convert the approximately radial rotary movement of the rod into an approximately axial rotary movement of the fixation member.

As a preference, the axial length of the fixation members is greater than the axial dimension of the intervertebral space, so that each of the said fixation members is formed of at least two fixation member parts implanted in turn, the said at least two fixation member parts interconnecting, particularly by snap-fastening.

As a preference, the said intermediate element comprises at least one moving and/or deformable element allowing relative movement between the said first and second rigid elements, to form an artificial discal articulation.

As a preference, the said at least one moving and/or deformable element defines a viscoelasticity, preferably an adjustable one.

Advantageously, the said viscoelasticity is adjustable after the fixator has been implanted, particularly by means controlled remotely from the outside.

According to one embodiment of the invention, the said at least one moving and/or deformable element comprises a bellows filled with liquid, particularly with silicone oil.

Advantageously, there are at least two bellows separate from one another, each bellows being filled with a respective determined amount of liquid, particularly silicon oil.

As an alternative, there are at least two bellows joined together, particularly via a valve, so that the liquid can pass from one bellows to the other, and vice versa.

Advantageously, the said at least one bellows is filled with liquid before, during and/or after implantation of the fixator, it being possible for the amount of liquid to be modified at any time after the fixator has been implanted.

Advantageously, the said fixator is implanted in the intervertebral space and fixed to the vertebrae via the conventional posterior vertebral route.

Advantageously the shape and/or dimensions, particularly axial, of the fixator are adapted, during the implantation, to suit the dimensions, particularly axial, of the intervertebral space.

Advantageously, the said fixator is designed to increase the axial dimensions of the intervertebral space to the maximum desirable height.

Another subject of the present invention is a vertebral fixator system comprising at least two vertebral fixators as defined hereinabove.

As a preference, a respective vertebral space contains at least two vertebral fixators.

Advantageously, the said at least two vertebral fixators have complementing exterior shapes so that once they have been implanted, they together form a geometrically coherent entirety capable of filling almost all of the intervertebral space.

Vertebral fixators may well be arranged in at least two intervertebral spaces, particularly adjacent ones.

According to an advantageous alternative form of the invention, the said vertebral fixators are connected to a posterior arrangement of fixators which is implanted in the posterior part of the vertebral column.

As a preference, the said connection is made by means of rods connecting the posterior arrangement of fixators to the fixation members of the said vertebral fixators.

Advantageously, the vertebral fixator system forms a total functional vertebral prosthesis for at least one vertebral stage, designed to provide simultaneous fixation and mobility of the facetiary posterior articulations and of the discal anterior articulations.

The invention will now be described in greater detail in the following detailed description of a number of embodiments and alternative forms which are given by way of non-limiting examples, with reference to the appended drawings, in which.

Figure 1:
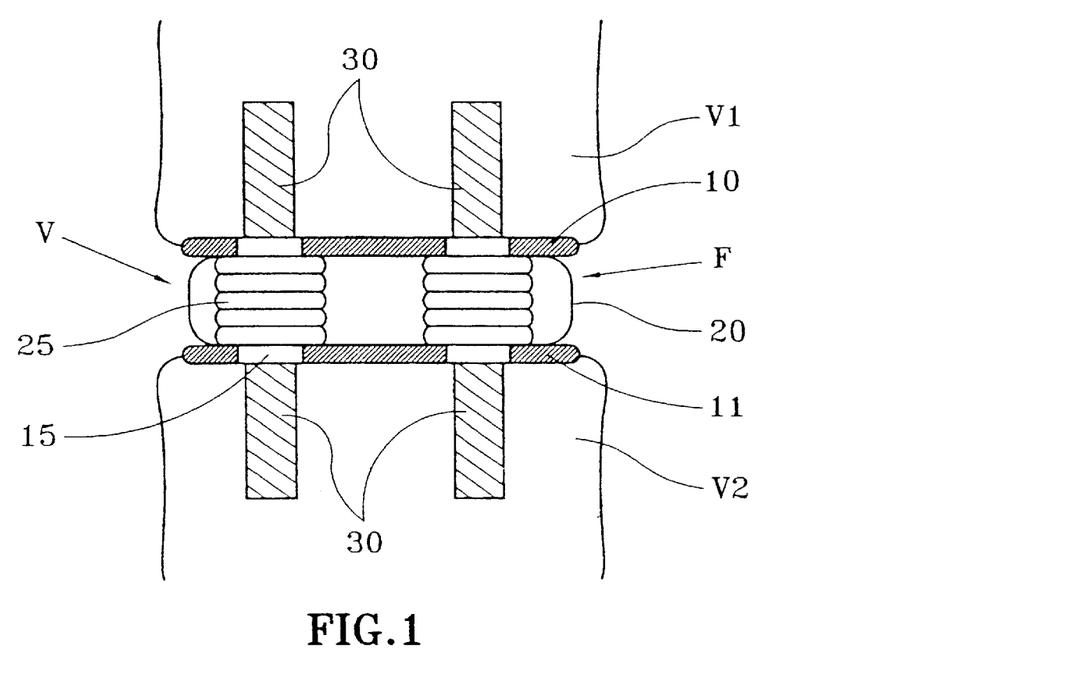
FIG. 1 is a diagrammatic view in section of an intervertebral fixator according to a particular embodiment of the invention.

Referring to FIG. 1, the fixator F comprises two essentially rigid plates 10, 11 fixed respectively to a vertebra V1, V2. The two plates 10, 11 are interconnected by one or more intermediate element(s) 20 comprising at least one, preferably two, moving and/or deformable elements 25, advantageously produced in the form of bellows filled with liquid, for example, silicon oil. Conceivable materials for the said plates and/or the said intermediate elements include, in particular, implantable stainless steel or titanium.

The two bellows 25 may be totally separate and independent, in which case each bellows is filled with a respective determined amount of liquid. The bellows 25 may also be joined together via a valve (not depicted) allowing liquid to pass from one bellows to the other, and vice versa. Advantageously the bellows 25 are filled, for example using a catheter, before, during and/or after implantation of the fixator in the intervertebral space V. The amount of liquid in each bellows 25 may advantageously be easily modified at any time after the fixator has been implanted, even several years later. This allows the characteristics of the fixator to be modified gradually, both as regards its size and as regards its articular capability (mobility, viscoelasticity). It might also be possible to provide small flexible feed tubes (not depicted) connecting the bellows to a subcutaneous element (not depicted), so that the amount of liquid can be varied very easily without surgical intervention, for example using a syringe. Furthermore, it is possible to provide implanted pressure sensors and remotely controlled means so that the articular parameters of the bellows can be modified from the outside, without changing the amount of liquid, but by modifying the distribution of the liquid in the bellows. Such remotely controlled means are described, in particular, in document EP-0820731 and U.S. applications Ser. Nos. 09/200885 and 08/897673 which are incorporated herein by way of reference as regards the form and operation of these remote control means.

Figure 2:
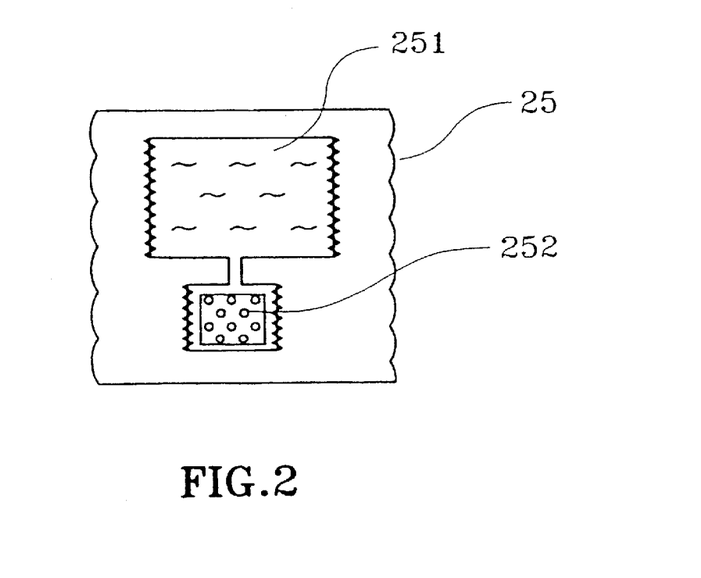
FIG. 2 is a very diagrammatic view of a bellows which can be used in the present invention.

The liquid-filled bellows 25 provide a viscoelasticity which makes for the artificial articulation of the fixator. With reference to FIG. 2, these bellows 25 may advantageously be designed in the manner of a damper and comprise a deformable liquid chamber 251 connected to an expansion/dilatation chamber 252. The expansion/dilatation chamber 252 may comprise compressible means, such as bubbles of gas or the like, so that supplying liquid to this chamber 252 allows the liquid chamber 251 and therefore the bellows 25 to be compressed. Of course, any equivalent type of arrangement is conceivable.

Other types of deformable member also allowing a variation in the viscosity and/or a various in the size, particularly in the axial direction of the thickness, of the deformable member, are described in the aforementioned European and American applications, for example in FIGS. 14 to 31 and the corresponding description and, in particular, as far as thickness variations are concerned, in FIGS. 40 to 47 and the corresponding description.

The deformable member or members, for example the bellows 25, may be connected, directly or via a high-pressure chamber, to a member 253 for refilling with fluid, for example a bellows acting in the manner of a pump and may be connected, for example, to the chamber or to the bellows 25 by a non return valve 254. A refill member such as this is described, for example, in FIG. 46 and 47 of patent applications EP-0820731 and U.S. application Ser. No. 09/200855 and its parent application, or in FIG. 64 and the corresponding description of application EP 0953317 and U.S. application Ser. No. 09/200855. The refill member operates like a pump arranged in a suitable location of the organism and actuated by movements thereof, as described in the aforementioned applications.

Figure 18:
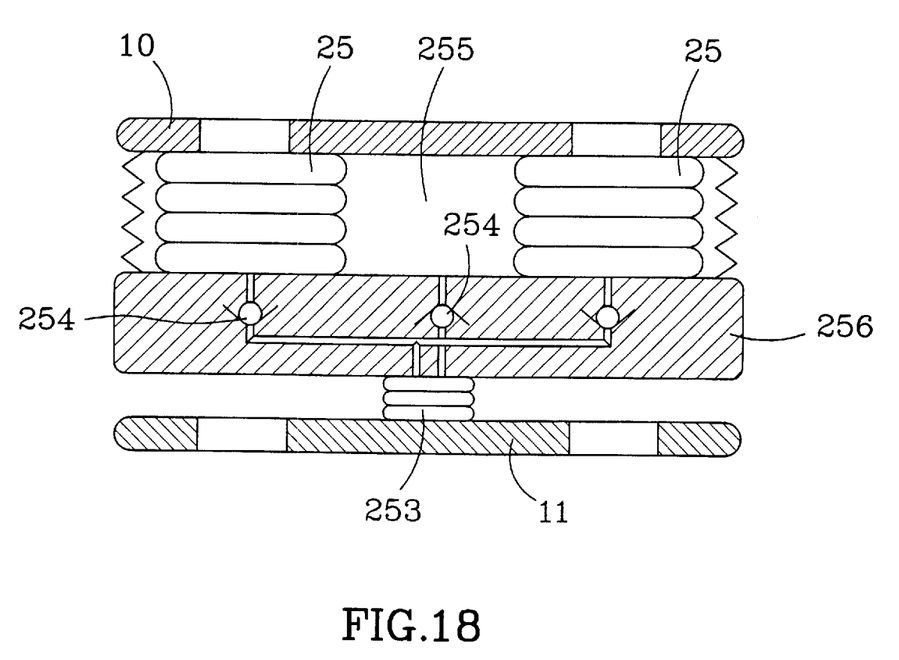

As a preference, as can be seen in FIG. 18 and in the manner of the aforementioned FIG. 64, the refill device is mounted on the fixator itself. The singular or plural bellows 25 and the refill member 253 are mounted in series through the insertion of a part 256 and operate as two differential pistons, the displacement of the refill member being very small. The small bellows, connected by a non-return valve 254 to a low-pressure reservoir 255 which, for example, collects the leaks from the deformable member and, via another non-return valve 254, to the deformable member or bellows 25 itself with a higher diameter, if necessary via an intermediate high-pressure chamber. As an option, the connection from the refill pump to the deformable member may include a control valve, but it is equally possible to omit such a valve and make a direct connection. Likewise, the connection between the deformable member and a low-pressure chamber may included a controllable valve, but this may equally be omitted so that the low-pressure chamber collects only any leaks that might come from the deformable member.

Very advantageously, a calibrated leak between the deformable member 25 and the low-pressure chamber or reservoir 255 may be deliberately introduced so that the deformable member empties gradually if the patient is at rest, the bellows then reducing in thickness and the intervertebral disc then reducing in thickness. On the other hand, if the patient is highly active, the high-pressure refill member fills the deformable bellows again and the thickness of the intervertebral fixator increases.

It must be clearly understood that an embodiment such as this comprising a deliberate leak can be used in skeletal implants other than the present intervertebral fixators, and, in particular, the various implants described in the aforementioned European and American applications.

Figure 3:
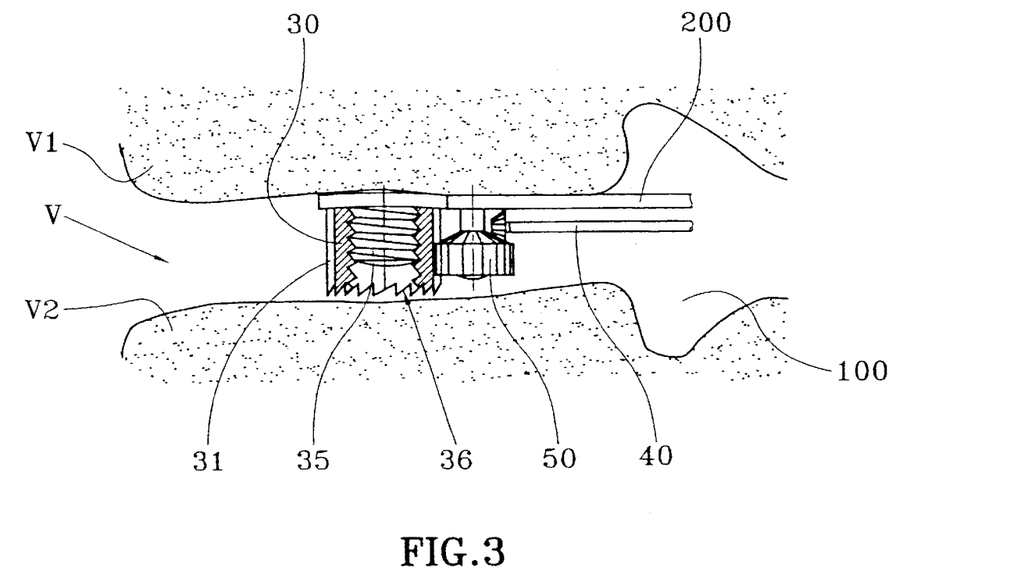
FIG. 3 is a diagrammatic view in section of the screwing means according to one embodiment of the invention.
Figure 4:
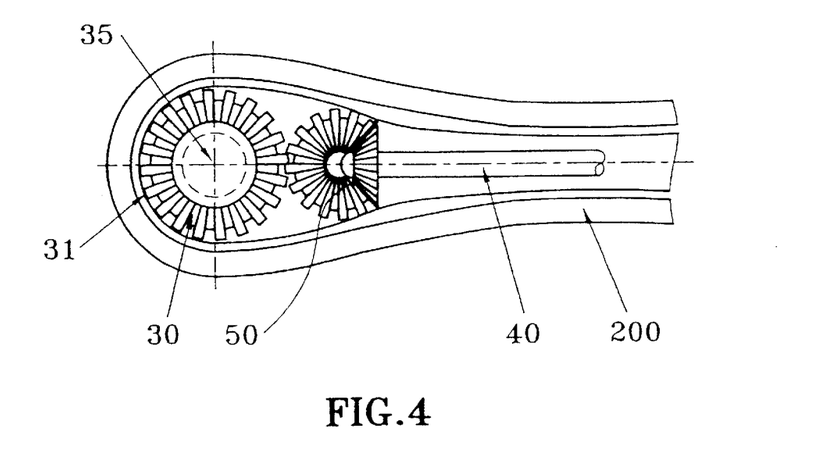
FIG. 4 is a diagrammatic view from below of the screwing means of the FIG. 3, FIGS. 5 and 6 diagrammatically show a fixation member consisting of two fixation member parts which snap-fasten together.
Figure 5:
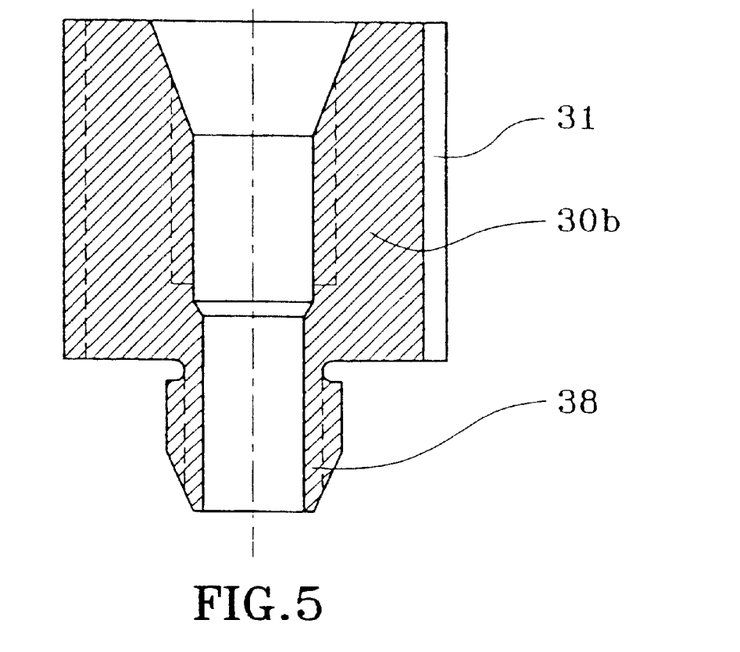
Figure 6:
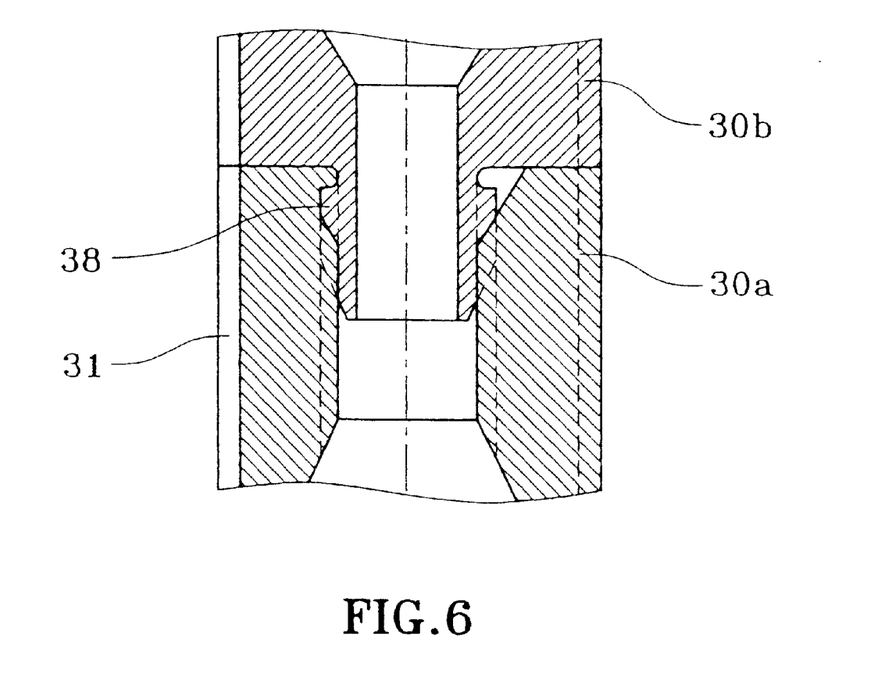

The fixing of the plates 10, 11 to the articular face of the respective vertebra V1, V2 is preferably achieved by fixation members 30, such as rods or screws, which are screwed into the vertebrae V1, V2 in a direction roughly at right angles to the articular faces of the vertebrae, through holes 15 provided for this purpose in the said plates 10, 11. As a preference two fixation members 30 are provided for each plate, so that each fixator has four fixation members. Referring to FIGS. 3 and 4, implantation is carried out by a posterior route through a roughly radial canal 100 created by the surgeon. The terms "radial" and "axial" used in this description refer to the longitudinal axis of the vertebral column, a radial canal therefore being roughly perpendicular to the said vertebral column. The use of conventional spinal posterior surgical routes is a great advantage because this makes it possible to avoid a major intervention by an anterior or lateral route. Once the intervertebral space V has been emptied, the plates 10, 11 are put in place through the said canal then fixed to the articular face of the respective vertebra V1, V2. To do this, the fixation members 30 are advantageously connected to a rotary rod 40 introduced through the said canal 100, possibly inside a guide element 200, an arrangement of rotary gearwheels 50 being provided on the discal end of the rod 40 to convert the radial rotary movement of the rod 40 into an axial rotary movement of the fixation members 30.

Advantageously, use may be made of a system of the boring type, in which the fixation member 30 is mounted on an internal insert 35 via a screw thread, the said insert being held stationary so that rotating the fixation member 30 entails moving it along the said insert 35 and therefore screwing it into the vertebra. As a preference, the fixation member 30 comprises external longitudinal ribs 31 to collaborate with the arrangement consisting of the gearwheel 50 and the screwing rod 40 and to transmit a motive rotation to the said fixation member. Other screwing systems are also conceivable.

Figure 12:
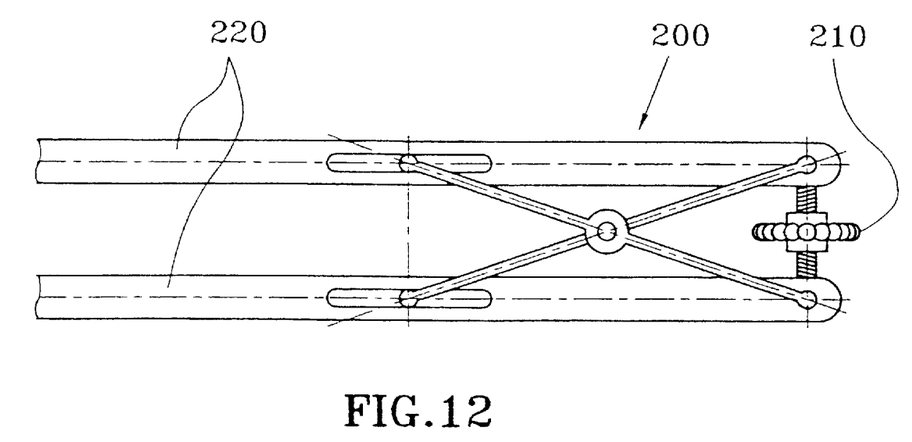
FIG. 12 is a diagrammatic view of a separator guide tube designed for the surgical implantation and/or explantation of the fixation members.

The guide element 200 is advantageously a separator device, as depicted in FIG. 12. By turning the knob 210, the walls 220 of the device are parted. Thus, once the guide element 200 has been introduced into the intervertebral space V through the canal 100, the two vertebrae V1 and V2 can be parted slightly to make implanting the fixator F easier.

Figure 7:
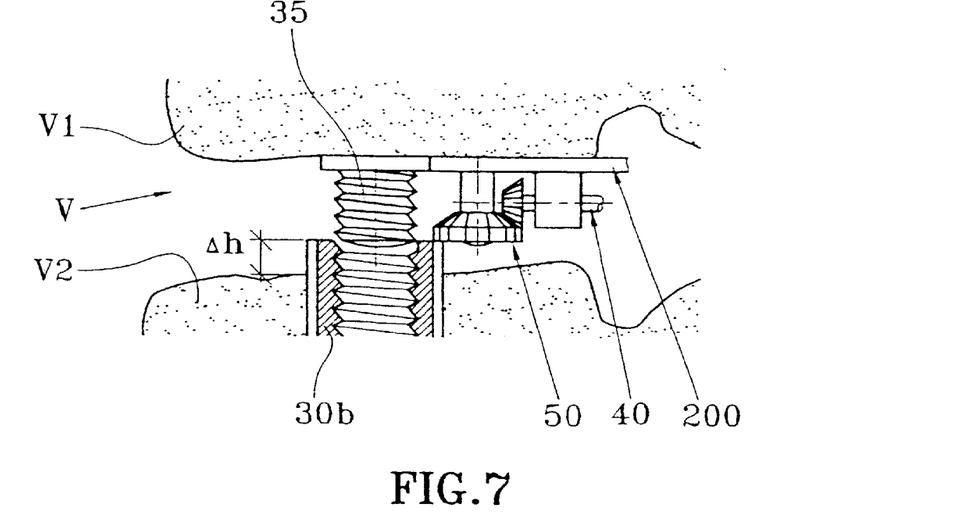
FIGS. 7 and 8 are diagrammatic views in section illustrating means for completely screwing the fixation member.
Figure 8:
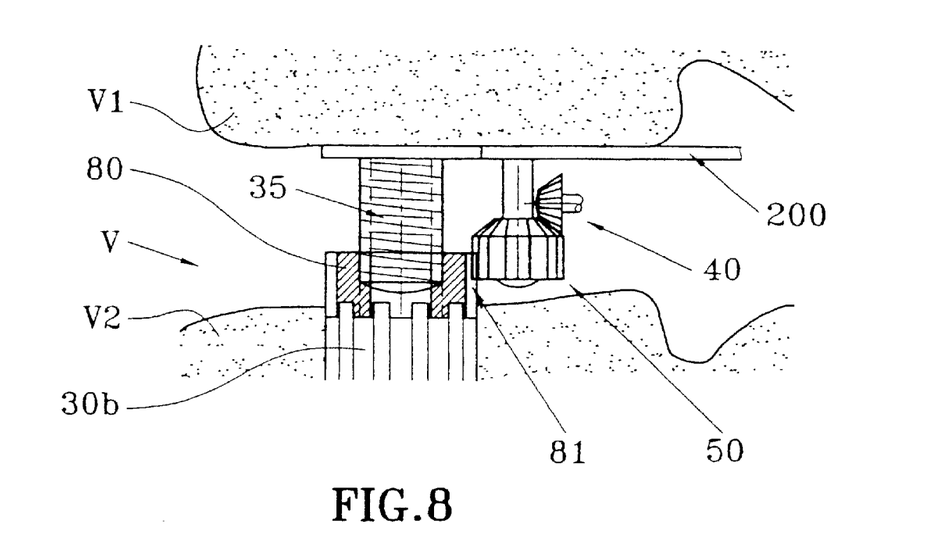
Figure 9:
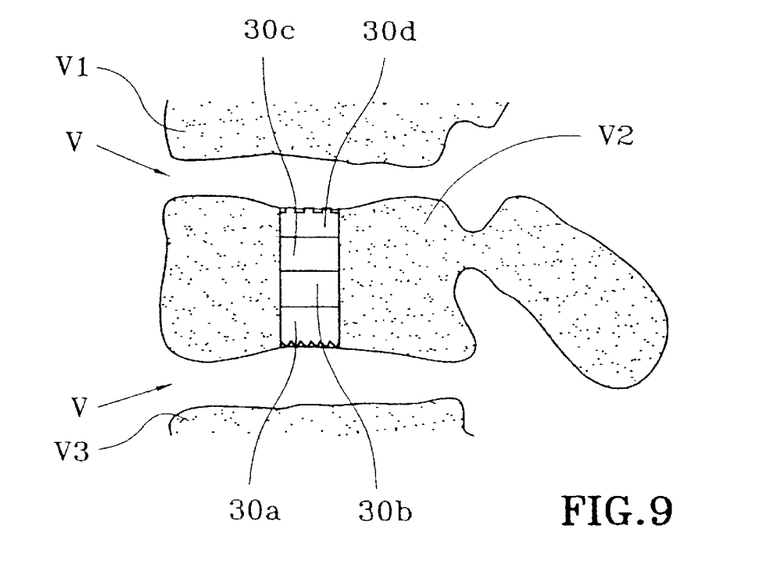
FIG. 9 is a diagrammatic view in section showing a vertebra comprising a fixation member made in four parts, FIGS. 10 and 11 diagrammatically show two different screwing ends for the fixation members.

In general, to ensure good fixation, the axial length of the fixation members 30 has to be greater than the axial dimension of the intervertebral space V. This also provides the vertebral column with additional strengthening. In this case, each fixation member 30 comprises at least two fixation member parts 30a, 30b which mechanically interconnect. An example is depicted in FIGS. 7 and 8 which show the snap-fastening together of the two fixation member parts 30a, 30b. The first fixation member part 30a is screwed into the vertebra until it is partially into the bone. The rod 40 is then removed and the second fixation member part 30b is arranged on the gearwheel arrangement 50 and brought up to face the rear end of the first fixation member part 30a. This rear end of the first fixation member part 30a and the front end of the second fixation member part 30b advantageously comprise snap-fastening means 38 which completely secure the two fixation member parts together. Rotating the second fixation member part 30b using the rod 40 therefore causes the first fixation member part 30a to rotate, and continues to screw it into the vertebra. Of course, it is possible to provide more than two fixation member parts, for example four parts 30a, 30b, 30c and 30d as depicted in FIG. 9.

Another advantage afforded by the fixation members 30 which have an axial dimension markedly greater than that of the intervertebral space V lies in the fact that the fixator of the invention can then also be used in the event of a fracture to one or more vertebrae. The fixation members 30 then allow the fractured vertebra to be fixed. The invention therefore also provides an intravertebral vertebral fixator which can be implanted via a posterior route.

It is equally possible to envisage other systems for securing the fixation member parts together. For example, the fixation member parts may connect together in some way other than by snap-fastening, for example by screw-fastening.

As an option, it is possible to envisage a different arrangement for screwing the last fixation member part, particularly for fully screwing the fixation member part 30. Specifically, referring in particular to FIG. 7, because of the non-zero axial dimension of the gearwheels 50, it may prove difficult or even impossible to get the fixation member 30 fully into the vertebra. To eliminate the height Δh projecting into the intervertebral space V, use may be made of a device as depicted in FIG. 8. This device comprises a screwing element 80 capable of collaborating removably with the rear end of the last fixation member part 30b. This screwing element 80 is preferably made in a similar way to the fixation member 30, with external ribs 81 to collaborate with the gearwheel arrangement 50, and is mounted on the insert 35. Interconnection between the screwing element 80 and the fixation member 30 may be achieved via toothing, as depicted in FIG. 8, but other appropriate means are conceivable. After the fixation member 30 has been fully screwed, the screwing element 80 is removed. As an alternative, use could also be made of a rib/groove system (not depicted), either the ribs or the grooves feature being provided on the last part of the screw and the other feature being provided on the screwing rod. of course, any other appropriate system for achieving such screwing is conceivable.

Of course, the invention is not restricted to the screwing means described hereinabove and the fixation members 30 may be screwed by any appropriate mechanical and/or hydraulic means. In particular, the mechanical screwing rod equipped with gearwheels and actuated by the surgeon may be replaced by a hydraulic member connected to means designed to convert the forces exerted by the said hydraulic member into an axial force for screwing the fixation members.

Figure 10:
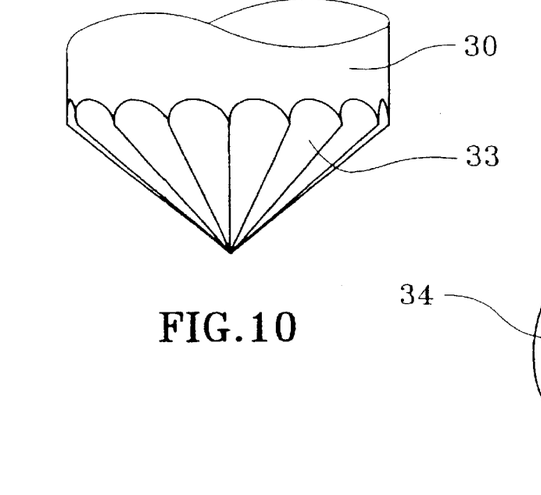
Figure 11:
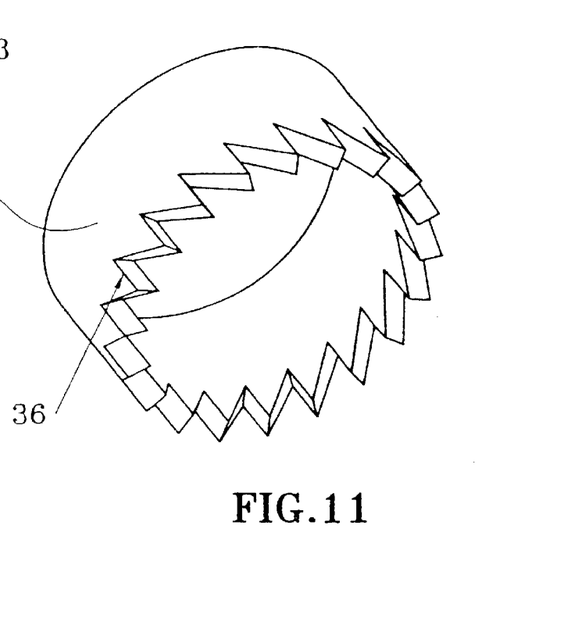

With reference to FIGS. 10 and 11, the front end of the fixation member 30, or of the first fixation member part 30a when several fixation member parts are provided, may have a spike 33 and be externally threaded. Advantageously, it is also possible to envisage a cylindrical shape 34 comprising, on the front edge, teeth 36 for biting into the bone during screwing, in the manner of a trepan. This makes screwing easier because the bone matter is removed to the inside of the fixation member, whereas in the case of an external screw thread, the bone matter is compressed, creating compression forces. In addition, the absence of an external thread makes it possible to provide the fixation members only with the external longitudinal ribs 31, which ensure perfect fixing into the vertebra and make possible explantation of the fixation members easier.

Figure 13:
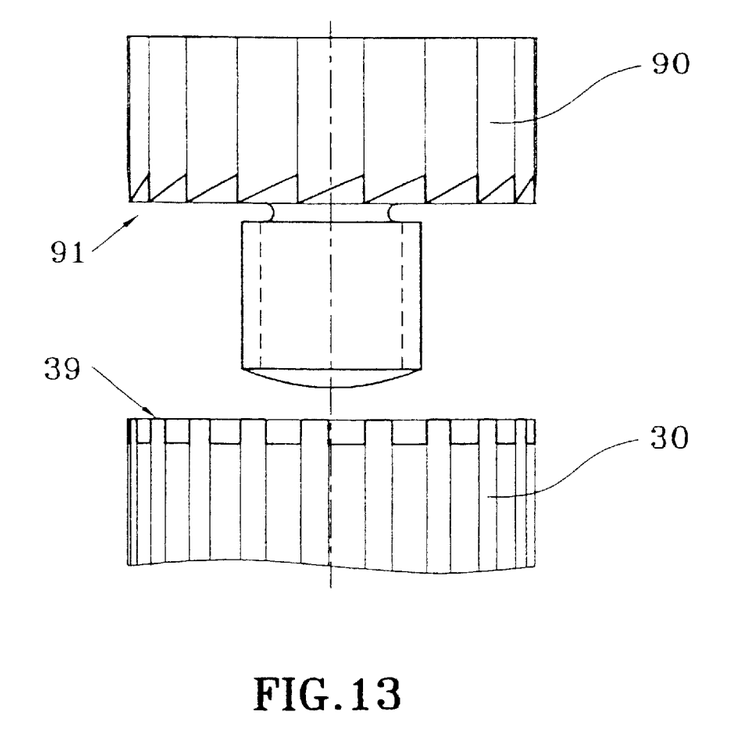
FIG. 13 is a diagrammatic view of explantation means for explanting the fixation members.

FIG. 13 very diagrammatically illustrates means which can be used to explant the fixation members 30, also via a posterior spinal route. These explantation means advantageously comprise an explantation element 90 similar to the screwing element 80 described hereinabove. This element 90 comprises gripping means 91, such as teeth, which can collaborate with the posterior edge 39 of the fixation member 30 to axially secure the two elements together. When the separator element 200, depicted in FIG. 12, is then separated, the explantation element 90 fixed to the said separator 200 drives the fixation member 30 axially out of the vertebra. Various gripping means 91 are conceivable, for example hooks or the like.

If necessary, particularly in the case of very serious pathology, it is possible to make the fixator of the invention substantially rigidly, without providing artificial articulation. In this case, it is possible to dispense with the moving and/or deformable elements. It is also possible to use bellows similar to those of the first embodiment hereinabove, replacing them with an amount of liquid which allows no movement. As an option, it might be possible to provide mechanical means of immobilization. Advantageously, when this is clinically desirable, it is then possible to reduce this amount of liquid after a certain length of time, and to restore to the fixator its articular function.

Figure 14:
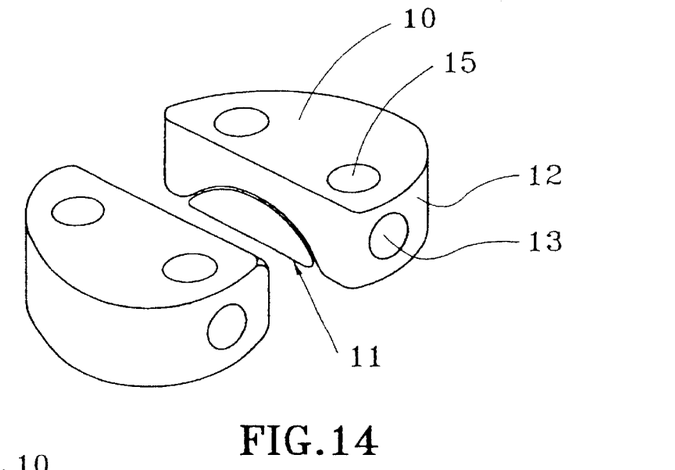
FIGS. 14 and 15 are diagrammatic views of two fixators according to another embodiment of the invention.

With reference to FIG. 14, the fixator F can be made "all-in-one", which means that the two plates 10, 11 and the bellows 25 (not visible) are introduced all together into the intervertebral space V. The plates 10, 11 then advantageously have lateral walls 12 with openings 13 for the passage of the screwing rod 40 10 (or the guide tube 200).

Two fixators F are generally provided in each intervertebral space V. In this case, each of the two fixators is implanted via the conventional right and left posterior routes, through a respective approximately radial canal made on each side of the vertebral column. The fixators of the invention are then implanted by the same routes as the aforementioned cages of the prior art.

Figures 15, 16:
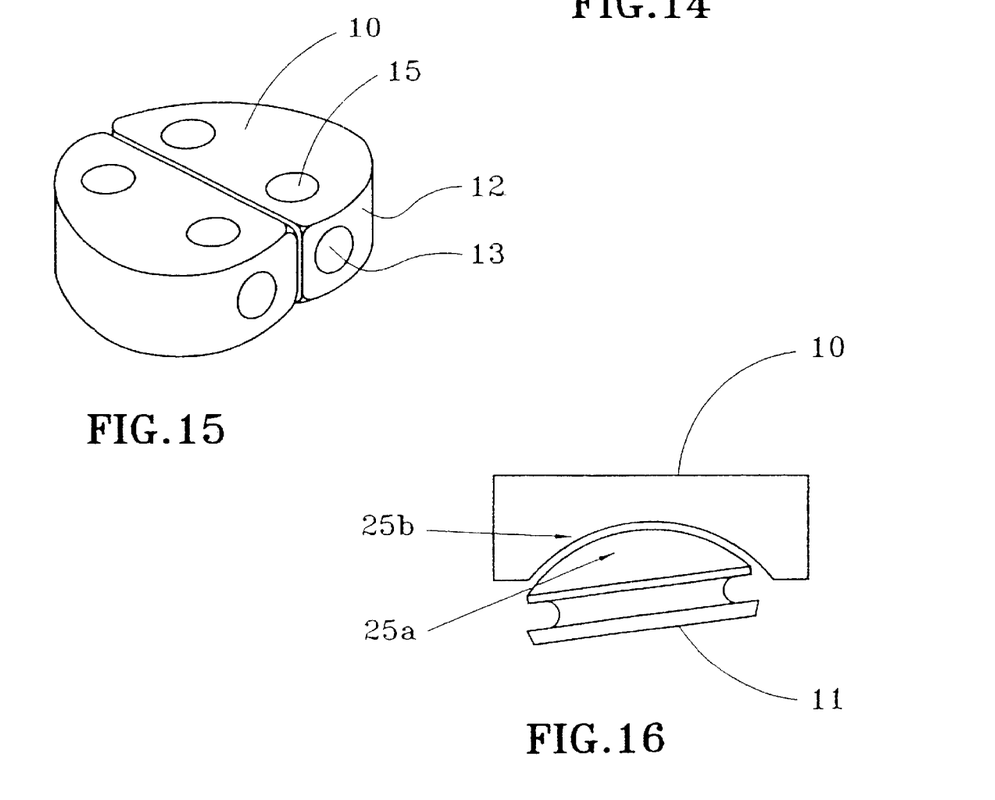
FIG. 16 is a fixator according to another alternative form of the invention, FIG. 17 diagrammatically shows a fixator system according to an advantageous embodiment of the invention, and FIG. 18 diagrammatically shows a fixator with a refill member.

With reference to FIGS. 14 and 15, the two fixators F advantageously have complementing shapes so that once they have been fitted, they can form a geometrically coherent entity, such as an all-in-one piece (FIG. 15). It is possible that more than two fixators might be provided in each intervertebral space, for example four fixators might be provided.

Figure 17:
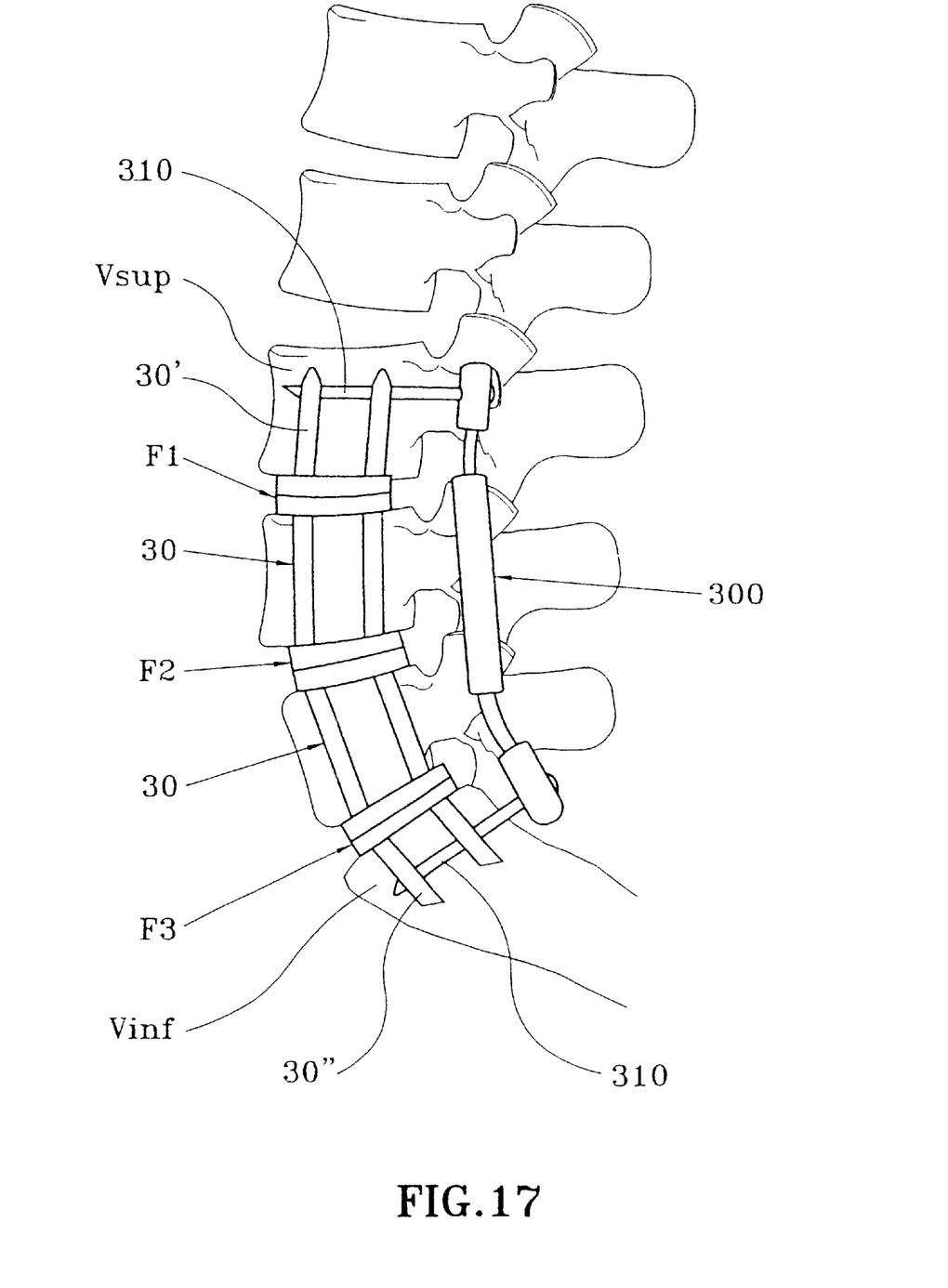

It is also possible to provide fixators F1, F2, F3 in several different intervertebral spaces, particularly adjacent intervertebral spaces as depicted in FIG. 17, which will be described in greater detail hereinafter.

The moving and/or deformable elements of the intermediate element may be produced in some form other than the form of bellows. Thus, as depicted diagrammatically in FIG. 16, it is possible to use complementary curved (convex or concave) surfaces 25a, 25b capable of sliding one on the other in a sliding space. It is also conceivable to interpose a moving sphere between two curved surfaces. It might be possible to introduce a viscoelasticity, for example providing a liquid in the sliding space. This viscoelasticity could be varied by connecting the sliding space to an expansion/dilatation chamber for the liquid or any another elastic element. This variation in viscoelasticity could be controllable, for example controlled remotely, from the outside. It is also possible to envisage making the moving and/or deformable elements of a compressible material, it being possible for the compression characteristics of the material to be predetermined and/or adjustable.

With reference to FIG. 17, the intervertebral fixators F of the invention can be connected with an arrangement or posterior fixators, for example of the moving adjustable type, as disclosed in documents EP-0 820 731 and FR-98 05549, which are incorporated herein by way of reference in relation to the operation of these posterior arrangements. In this case, this connection is advantageously made by connecting the arrangement of posterior fixators 300 to the fixation members 30 of the intervertebral fixators F, for example using rods 310. If a number of adjacent intervertebral spaces V of the vertebral column contain fixators F1, F2, F3, the connection with the posterior arrangement 300 is preferably made only at the fixation members 30' and 30" arranged respectively in the vertebrae Vsup and Vinf axially furthest apart, as depicted in FIG. 17. In this particular instance, in the example depicted, Vinf corresponds to the sacrum and Vsup corresponds to lumbar vertebra L3. Advantageously, when intervertebral fixators F1 and F2 are implanted in two adjacent intervertebral spaces, provision may be made for the fixation members 30 provided in the vertebra separating the said two adjacent intervertebral spaces to act as common fixation members for the two fixators F1 and F2. In this case, these fixation members may be implanted partially through the two intervertebral spaces, or entirely through just one of these intervertebral spaces. The latter scenario is illustrated in particular in FIG. 9, in which the entirety of the fixation member 30 is implanted in the vertebra V2 via the intervertebral space V until the first fixation member part 30a protrudes into the adjacent intervertebral space V'.

The combination of an adjustable posterior arrangement 300 and of intervertebral fixators F affords a complete artificial articulation simultaneously replacing the posterior facetary vertebral articulations and the anterior discal articulation of one and the same vertebral stage, something which is impossible to achieve with the fixator devices hitherto known. It might also be possible to provide a connection between the bellows of the intervertebral fixators and the bellows of the adjustable posterior arrangement. This gives a great degree of modularity which allows precise tailoring to suit certain specific requirements.

Other modifications and alternative forms are conceivable without departing from the context of the present invention, the scope of which is defined the appended claims.

What is claimed is:

1. Vertebral fixator forming a discal prosthesis having substantially the height of an intervertebral disk to be replaced comprising at least one essentially rigid first element (10) intended to be fixed to the articular face of one (V1) of two adjacent vertebrae, and at least one essentially rigid second element (11) fixed to the articular face of the other vertebrae (V2), the said essentially rigid first and second elements (10, 11) being connected by at least one intermediate element (20) having articular mobility, the said essentially first and second elements and the said intermediate element being shaped dimensionally for introduction into the intervertebral space via a posterior or lateral surgical route, the said essentially rigid first and second elements having fixation members (30) capable, once the fixator has been arranged in the intervertebral space, of protruding from the two rigid elements (10, 11) essentially at right angles to their surfaces in contact with the corresponding surface of the vertebral body, in order to penetrate the vertebral body.

2. Vertebral fixator according to claim 1, in which the axial length of the fixation members (30) is greater than the axial dimension of the intervertebral space (V), so that each of the said fixation members (30) is formed of at least two fixation member parts (30a, 30b) implanted in turn, the said at least two fixation member parts (30a, 30b) interconnecting, by snap-fastening.

3. Vertebral fixator according to claim 1, in which the said fixator (F) is designed to increase the axial dimensions of the intevertebral space (V) to the maximum desirable height.

4. Vertebral fixator according to claim 1, in which the said essentially rigid first and second elements are plates (10, 11) comprising holes (15), the said plates (10, 11) each being arranged in the intervertebral space (V) against the articular face of a respective vertebra (V1, V2) so that the fixation members (30) such as rods or screws are passed through the said holes (15) and fixed, particularly screwed, into the respective vertebra (V1, V2).

5. Vertebral fixator according to claim 4, in which the fixation members (30) are screwed by means of a rotary rod (40) introduced approximately radially into the intevertebral space (V), a system of rotary gearwheels (50) being provided to convert the approximately radial rotary movement of the rod (40) into an approximately axial rotary movement of the fixation member (30).

6. Vertebral fixator according to claim 1, in which said intermediate element is a moving and/or deformable element (25) inserted between the said essentially rigid elements, said elemement defining viscoelasticity.

7. Vertebral fixator according to claim 6, in which the said viscoelasticity is adjustable after the fixator has been implanted, by means controlled romotely from the outside.

8. Fixator according to claim 1, characterized in that it comprises, between the said essentially rigid elements (10, 11), deformable or expandable means making it possible to increase the thickness of the intervertebral prosthesis formed by the fixator.

9. Fixator according to claim 8, characterized in that it comprises adjusting means to allow the fixator to be expanded.

10. Fixator according to claim 8, characterized in that the expandable means comprise an element which can be deformed under the action of a fluid.

11. Vertebral fixator according to claim 10, in which the said at least one moving and/or deformable element comprises a fluid-filled bellow (25).

12. Vertebral fixator according to claim 11, in which said bellows (25) is filled with fluid before, during and/or after implantation of the fixator (F), it being possible for the amount of fluid to be modified at any time after the fixator (F) has been implanted.

13. Vertebral fixator according to claim 11, in which there are at least two bellows (25) separate from one another, each bellows being filled with a respective determined amount of fluid.

14. Vertebral fixator according to claim 13, in which there are at least two bellows (25) joined together, via a valve, so that the fluid can pass from one bellows to the other, and vice versa.

15. A vertebral forming a discal prosthesis having substantially the height of an intervertebral disk to be replaced comprising at least one essentially rigid first element (10) intended to be fixed to the articular face of one (V1) of two adjacent vertebrae, and at least one essentially rigid second element (11) fixed to the articular face of the other vertebrae (V2), the said essentially rigid first and second elements (10, 11) being connected by at least one intermediate element (20) having articular mobility, the said essentially first and second elements and the said intermediate element being shaped dimensionally for introduction into the intervertebral space via a posterior or lateral surgical route, the said essentially rigid first and second elements having fixation members (30) capable, once the fixator has been arranged in the intervertebral space, of protruding from the two rigid elements (10, 11) essentially at right angles to their surfaces in contact with the corresponding surface of the vertebral body, in order to penetrate the vertebral body comprising between the said essentially rigid elements (10, 11), deformable or expandable means making it possible to increase the thickness of the intervertebral prosthesis formed by the fixator and the expandable means comprise an element which can be deformed under the action of a fluid, it comprises means of pressurizing fluid under the action of bodily forces in order to refill the said deformable element with pressurized fluid.

16. Fixator according to claim 15, characterized in that the refilling means are carried by the fixator.

17. A vertebral fixator according to claim 15 wherein a fluid leakage from said expandable means progressively whereby it reduces in thickness if the patient is inactive, while said means of pressurizing fluid provokes said expandable means to increase in thickness if the patient is active.

18. Vertebral fixator system, characterized in that it comprises at least two vertebral fixators (F).

19. Vertebral fixator system according to claim 18, in which a respective vertebral space (V) contains at least two vertebral fixators (F).

20. Vertebral fixator system according to claim 19, in which the said at least two vertebral fixators (F) have complementing exterior shapes so that once they have been implanted, they together form a geometrically coherent entity capable of filling almost all of the intervertebral space (V).

21. A vertebral fixator system having at least two vertebral fixators (F), in which the said vertebral fixators (F) are connected to a posterior arrangement (300) of fixators which is implanted in the posterior part of the vertebral column.

22. Vertebral fixator system according to claim 21, in which the said connection is made by means of rods (310) connecting the posterior arrangement (300) of fixators to the fixation members (30) of the said vertebral fixators (F).

23. A method for implanting an inter-vertebral fixator replacing an inter-vertebral disc between two adjacent vertebral bone bodies comprising the steps of preparing at least one posterior or lateral surgical approach to the intervertebral space between said bodies, removing the intervertebral disc if needed, introducing through said posterior or lateral surgical approach a discal prosthesis comprising at least one essentially rigid first element (10) intended to be fixed to the articular face of one (V1) of two adjacent vertebrae, and at least one essentially rigid second element (11) fixed to the articular face of the other vertebra (V2), the said essentially rigid first and second elements (10,11) being connected by at least one intermediate element (20) having an articular property, the said essentially rigid first and second elements and the said intermediate element being shaped dimensionally for introduction into the intervertebral space via a posterior or lateral surgical route, the said essentially rigid first and second elements having fixation members (30) capable, one the fixator has been arranged in the inter-vertebral space, of protruding from the two rigid elements (10,11) essentially at right angles to their surfaces in contact with the corresponding surface of the vertebral body and then to move said fixations members (30) to protrude from said two rigid elements (10,11) in order to penetrate said vertebral bodies.

* * * * *